US006986779B2

(12) United States Patent
Begley

(10) Patent No.: US 6,986,779 B2

(45) Date of Patent: Jan. 17, 2006

(54) PAIN RELIEVING PRESSURE MAINTENANCE APPARATUS AND METHOD

(76) Inventor: Ricky Lee Begley, deceased, late of Miami, FL (US); by Karen Begley, legal representative, 14225 SW. 103rd Ave., Miami, FL (US) 33176

(*) Notice: Subject to any disclaimer, the term of this patent is extended or adjusted under 35 U.S.C. 154(b) by 0 days.

(21) Appl. No.: 10/868,401

(22) Filed: Jun. 15, 2004

(65) Prior Publication Data

US 2004/0254505 A1 Dec. 16, 2004

Related U.S. Application Data

(60) Provisional application No. 60/488,228, filed on Jul. 17, 2003, provisional application No. 60/478,858, filed on Jun. 16, 2003.

(51) Int. Cl.
*A61H 39/04* (2006.01)
*A61B 17/08* (2006.01)

(52) U.S. Cl. ...................... 606/204; 606/202; 601/148; 601/151; 602/21; 602/53

(58) Field of Classification Search ................ 606/202, 606/204; 602/53

See application file for complete search history.

(56) References Cited

U.S. PATENT DOCUMENTS

| | | | | |
|---|---|---|---|---|
| 5,199,876 | A * | 4/1993 | Waldman | 434/262 |
| 5,405,310 | A * | 4/1995 | Yoo | 601/134 |
| 5,405,357 | A * | 4/1995 | Rowe-Lanzisera et al. | 606/204 |
| 5,695,520 | A * | 12/1997 | Bruckner et al. | 606/204 |
| 5,709,647 | A * | 1/1998 | Ferber | 601/134 |
| 6,152,140 | A * | 11/2000 | Blum | 128/898 |
| 6,214,027 | B1 * | 4/2001 | Brossard | 606/201 |
| 6,277,142 | B1 * | 8/2001 | Pinter | 607/1 |

FOREIGN PATENT DOCUMENTS

JP 2000033107 A * 2/2000

* cited by examiner

*Primary Examiner*—Danton DeMille

(74) *Attorney, Agent, or Firm*—Fleit, Kain, Gibbons, Gutman, Bongini & Bianco P.L.

(57) ABSTRACT

A glove that when worn by a user quickly, comfortably, conveniently and effectively applies a specific amount of pressure to a particular point on the wearer's hand, thereby relieving and/or eliminating pain of the wearer such as from a type of headache. A glove worn by the person with pain, such as a headache, includes an internal pressure point applicator and an inflatable bladder to apply pressure to a desired point on the wearer's hand.

15 Claims, 16 Drawing Sheets

PAIN RELIEVING PRESSURE MAINTENANCE APPARATUS AND METHOD

CROSS-REFERENCE TO RELATED APPLICATIONS

This application is based upon and claims priority from prior U.S. patent application Ser. No. 60/478,858, filed Jun. 16, 2003, and U.S. patent application Ser. No. 60/488,228, filed Jul. 17, 2003, the entire disclosures of which are herein incorporated by reference.

BACKGROUND OF THE INVENTION

1. Field of the Invention

The present invention generally relates to pain relieving devices and more particularly, the present invention relates to a method and apparatus for relieving pain by applying pressure to a particular pressure point of the body.

2. Description of Related Art

The medical industry has long tried to help people control their pain. The only problem is that with most chronic pain or illness, there is no cure. With most medications, people also have to deal with the side effects. The medical industry continues to develop and prescribe medication to help the general public. One of their main strengths is that people will do almost anything to relieve pain. Headaches are the most common pain that we have to deal with almost everyday. According to several health insurance companies, two-thirds of headache sufferers are women. Migraines are documented as one of the most common types of headaches. A doctor will usually diagnose a migraine based on the history of symptoms. In most cases, a physical and neurological examination will be entirely normal. Despite years of research, scientists still do not know exactly why migraines occur. Most people who develop migraines will continue to have intermittent headaches over years. According to the National Headache Foundation, most people who suffer from migraines do not need to see a doctor. A typical migraine sufferer will have several attack each month, lasting anywhere from hours to days. Tension headaches are also one of the top two headaches that people suffer from on a consistent basis. Tension headaches are related to excessive and/or constant stress. Stress is becoming a natural part of our lives, and for the most part, must be dealt with. Dealing with stress in any manner can still cause mild tension headaches that can affect our daily activities. There are thousands of Headache Support Groups across the US helping people deal with chronic headaches. People who are hyper sensitive to medication of any type simply have lost control of their ability to live a normal functional life. The cure can be as debilitating as the pain in most cases.

Current Solutions

What solutions do people currently have? There are over-the-counter pain relievers, such as Tylenol, Advil, Motrin, etc. There are also shots like Immitrex and others that people can inject themselves or get at a hospital or doctor's office. The costs are high and consistent, and all of these have some type of side effect, especially to people who are sensitive to pharmaceuticals; even Tylenol can put people to sleep for a few hours. To summarize the prior art headache remedies and their characteristics:

a) Pharmaceuticals: (Over the counter.)
  1) Side effects: (Stomach problems, tiredness, and depression)
  2) Consistent costs
  3) 30 to 60 minutes for relief 4) Less effective day
  5) Time Consuming b) Hospitals:
  1) Time consuming
  2) Expensive
  3) Loss of the day, possibly 2 or 3.
  4) Follow up tests
  5) Future days lost
  6) Answer: Medication
  7) Side effects
  8) Less effective day c) Doctors Office Visit:
  1) Appointment date: (Usually days later)
  2) Time consuming: literally hours most of the time
  3) Loss of the day
  4) Schedule tests
  5) Loss of future days.
  6) Return to doctor's office for test results.
  7) Loss of another day.
  8) Side effects from the medication.
  9) Less effective days due to side effects.
  10) Make another appointment with the doctor.
  11) Lose another day in the doctor's office.
  12) Hope that the new medication works.

d) Rest:
  1) It works.
  2) It's free.
  3) It's safe.
  4) Doesn't have any side effects.
  5) The only problem is the ultimate problem. It's time consuming.

Western & Eastern/Drugs or Alternatives

The general public has the right to choose any method of pain relief that they want, and they are basically becoming more educated to their options as time continues. The more educated the general public becomes, the more successful alternative medicine will become. The pharmaceutical companies continue to develop medicines to alleviate pain as long as the doctors continue to prescribe them. Side effects are becoming more acceptable to those who have lost any hope of being pain free.

Since there is no scientific evidence explaining why people get migraines, then every time that a doctor prescribes a medication for this type of headache, he is testing it. We become the lab rat. Currently the industry evolves around treating the symptom and not the person as a whole. Scientifically there isn't always an answer for our symptoms that can be explained or researched under a microscope. This statement is the foundation of Eastern medicine.

The present solution to pain is rest. The entire industry is working to relieve pain, but practically all of their answers force you to slow down, or rest, (sort of ironic) because of the side effects of other treatments. The idea is to relieve pain so that you can continue to live a normal life, not to reduce the amount of time you have to actually live. The number one question currently at the top of the priority list for all of the industry is; "How can we help people control their pain without taking away from their life?"

SUMMARY OF THE INVENTION

The present invention provides relief from pain by providing a glove that is designed to quickly, comfortably, conveniently and effectively apply a specific amount of pressure to a particular point, relieving and/or eliminating the pain of any type of headache within minutes.

BRIEF DESCRIPTION OF THE DRAWINGS

The foregoing and other features and also the advantages of the invention will be apparent from the following detailed description taken in conjunction with the accompanying drawings.

DESCRIPTION OF THE PREFERRED EMBODIMENTS

An exemplary embodiment of the present invention is described herein and is shown in the figures. This exemplary embodiment is referred to by the name "The Headache Glove" (hereinafter also referred to as "glove"). The most common pains that we deal with on a daily basis are headaches. These headaches range from different levels of intensity to different types of pain. The glove can be used conveniently and comfortably as you carry on with your daily activities. The current design of the glove is practical and effective and has been reached through consistent testing and redesigning of the components of the glove. In general, acute headaches require time-consuming solutions, whereas the glove was specifically designed to save time by using the glove when needed while performing your daily obligations. Even though pressure point application to specific areas has been around for over a thousand years, the ability to apply constant pressure to a pressure point long enough to have an effect has always required time and assistance. The glove is designed to be used anywhere and at anytime without any assistance. Currently there are some devices designed to apply pressure, but the effectiveness is superficial and short-term. The glove, according to the present example, uses a Pressure Point Applicator ("PPA") that is pressed into a desired point on the wearer's hand by a bladder internal to the glove shell.

Glove Construction

Figure 1:
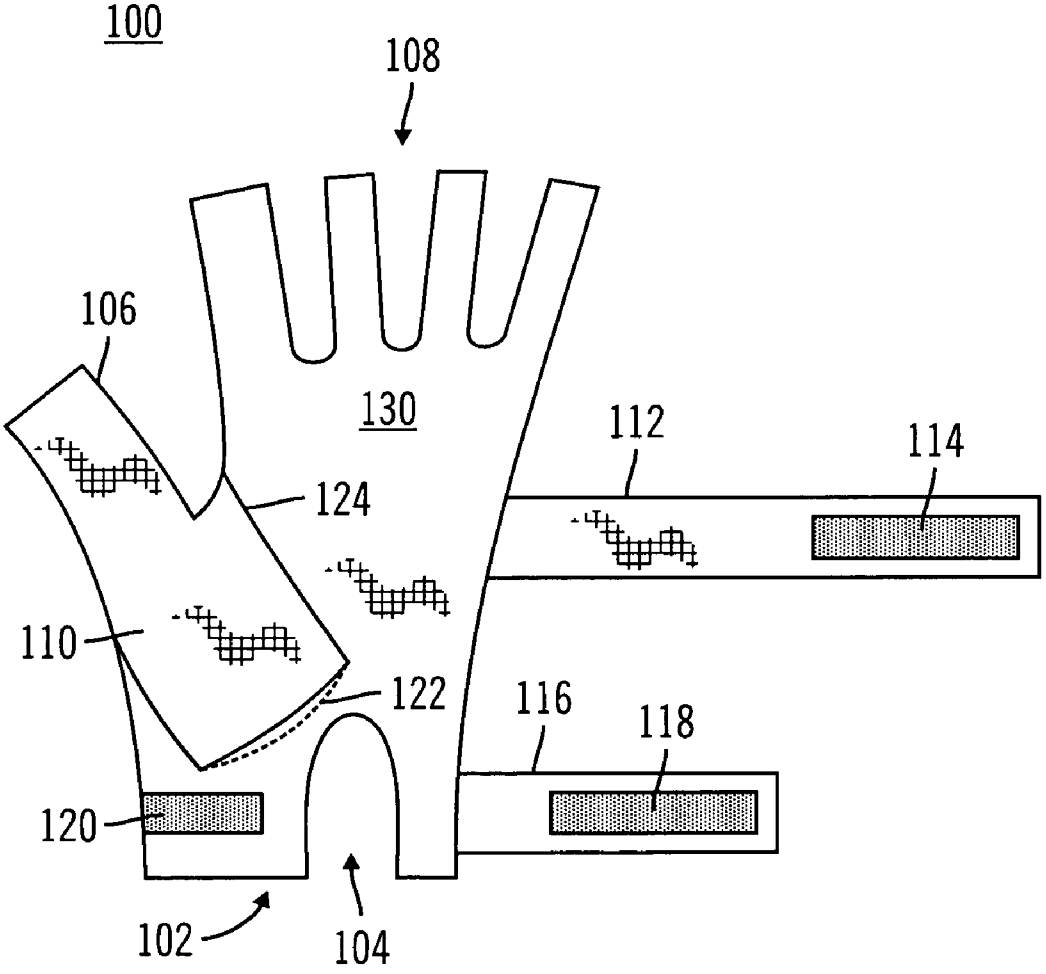
FIG. 1 illustrates a glove back view with open wrist straps according to an exemplary embodiment of the present invention.

FIG. 1 illustrates a glove back view 100 with open wrist straps according to an exemplary embodiment of the present invention. The glove back view 100 illustrates a glove 130 that has an outline similar to a conventional, open fingered glove. The glove back view 100 illustrates four open finger tubes 108 and a thumb tube 106. The glove 130 has a wrist opening 102 that allows a user to insert his or her hand into the glove 130. The glove back 132 also has a wrist slot 104 along the wrist opening 102 to facilitate placing the glove 130 onto a user's hand and similarly removing the glove. Two straps, a wrist strap 116 and a palm strap 112 are attached to the glove 130. The wrist strap 116 has a wrist strap Velcro strip 118 and the palm strap 112 has a palm strap Velcro strip 114. The wrist strap Velcro strip 118 attaches to a wrist section Velcro strip 120 as described below. These two straps allow properly fitting the glove 130 to a user's hand, as is described below.

Glove 130 further includes a pouch 110. Pouch 110 of the exemplary embodiment accepts a bladder and Pressure Point Applicator (PPA), as is described below. Pouch 110 is formed by a pouch patch that is placed inside the glove 130 and that is sewn to the glove 130 along stitching 124. Pouch 110 has a pouch opening 122 along the side of pouch 110 that is closest to the wrist opening 102. This pouch opening 122 allows a bladder and PPA to be inserted and removed from the glove 130.

Figure 2:
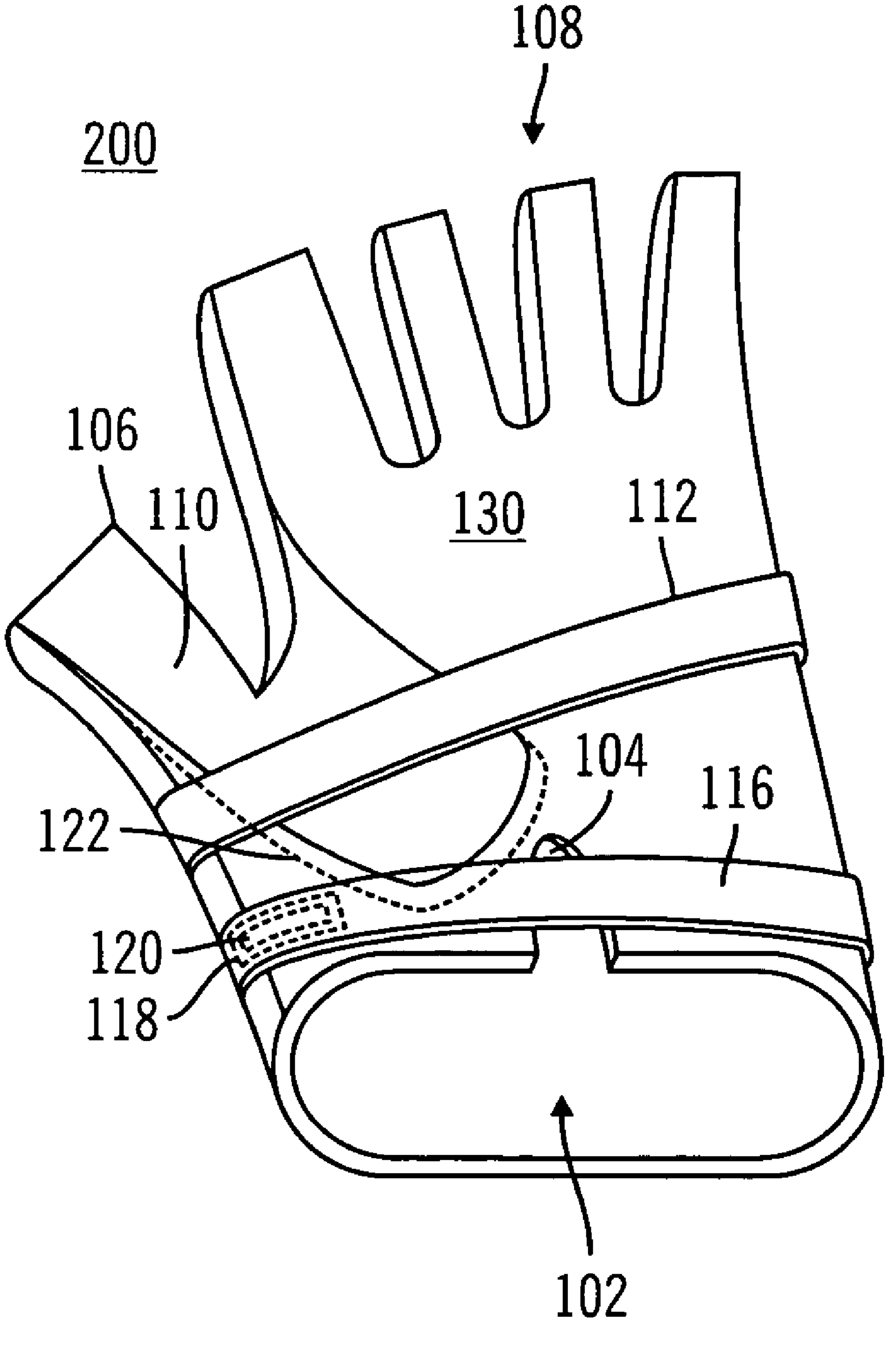
FIG. 2 illustrates a closed strap glove back view in accordance With the exemplary embodiment of the present invention.

FIG. 2 illustrates a closed strap glove back view 200 in accordance with the exemplary embodiment of the present invention. The closed strap glove back view 200 shows the wrist strap 116 closed along the bottom of the glove and the wrist strap Velcro strap 118 is attached to the wrist section Velcro strip 120. The closed strap glove back view 200 further illustrates the palm strap 112 placed across the back of the glove 130, including across pouch 110 in order to allow the bladder and PPA within pouch 110 to place adequate pressure onto the proper point of the user's hand, as is described below.

Figure 3:
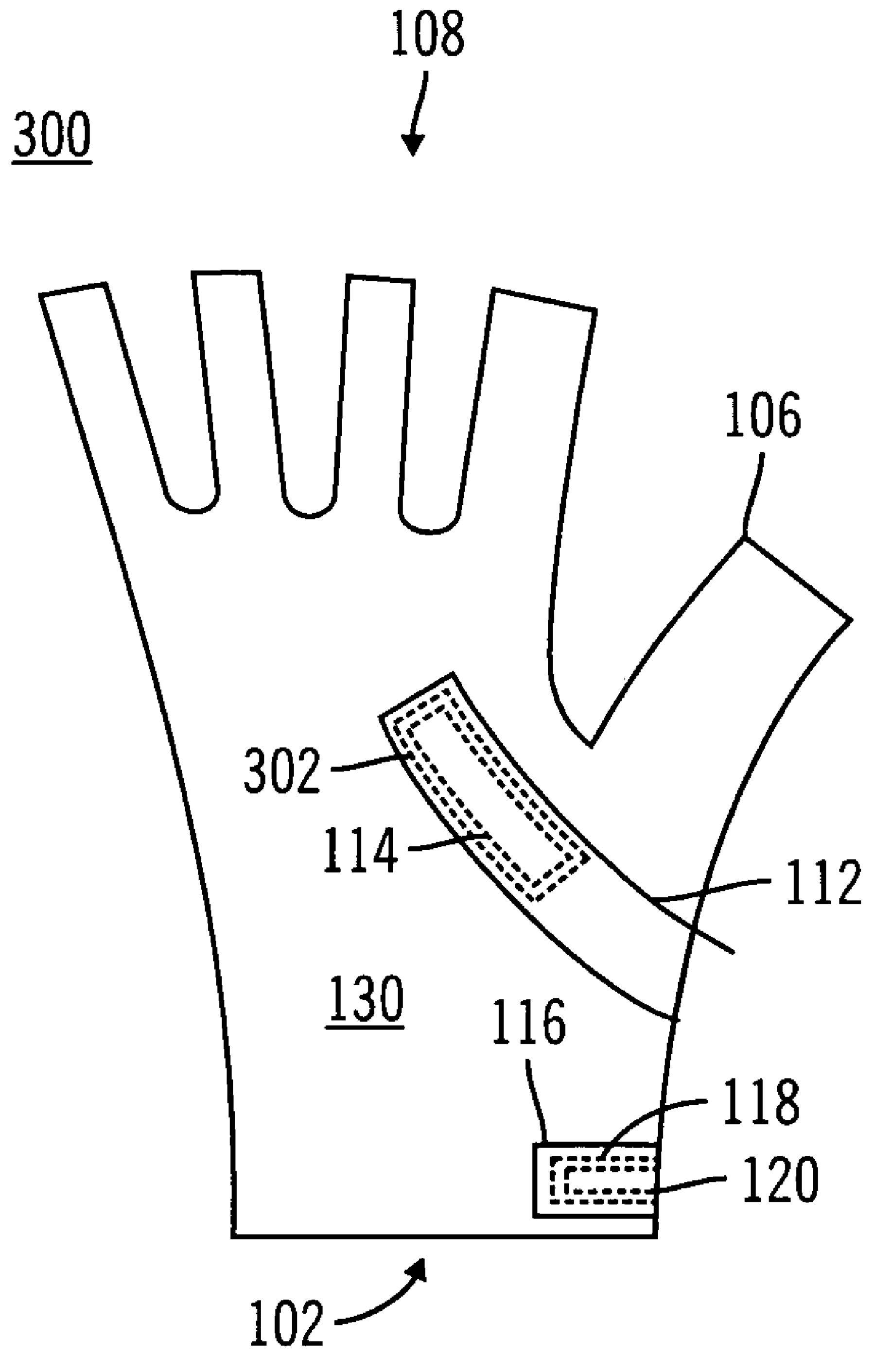
FIG. 3 illustrates a closed strap glove palm view in accordance with the exemplary embodiment of the present invention.

FIG. 3 illustrates a closed strap glove palm view 300 in accordance with the exemplary embodiment of the present invention. The closed strap glove palm view 300 illustrates that the palm strap 112 wraps around the user's thumb. The palm strap Velcro strip 114 is further shown as attached to a palm section Velcro strip 302. The wrist strap 116 of the exemplary embodiment is further shown as wrapping around to the palm side of glove 130, where the wrist strap Velcro strip 118 attaches to the wrist section Velcro strip 120.

Figure 4:
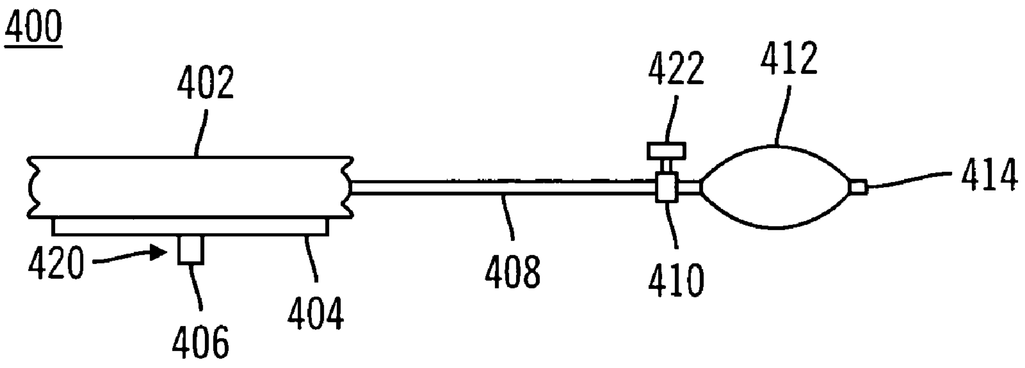
FIG. 4 illustrates a bladder and Pressure Point Applicator (PPA) in accordance with the exemplary embodiment of the present invention.

FIG. 4 illustrates a bladder and Pressure Point Applicator (PPA) 400 in accordance with the exemplary embodiment of the present invention. The bladder and Pressure Point Applicator (PPA) 400 has a bladder 402 that is an expandable rubber bladder that expands as air pressure within bladder 402 is increased. Bladder 402 further includes a Pressure Point Applicator 420 that includes a button 406 and a applicator base 404. Bladder 302 is attached to a pump 412 via a tube 408 and valve 410. Pump 412 of the exemplary embodiment is a compressible rubber bulb type pump similar to pumps used with blood pressure measurement cuffs. Pump 412 includes a check valve 414 to allow air to enter the pump 412 when the pump 412 is expanding and prevent air from leaving the pump 412 through check valve 414 when the pump 412 is compressed. Valve 410 allows air to be selectably released from an inflated bladder 402, such as when use of the glove 130 of the exemplary embodiment is completed. Pump 412 operates the bladder 402 by pumping air into bladder 402, thereby causing bladder 402 to expand and apply yieldable pressure, as is described below.

Figure 5:
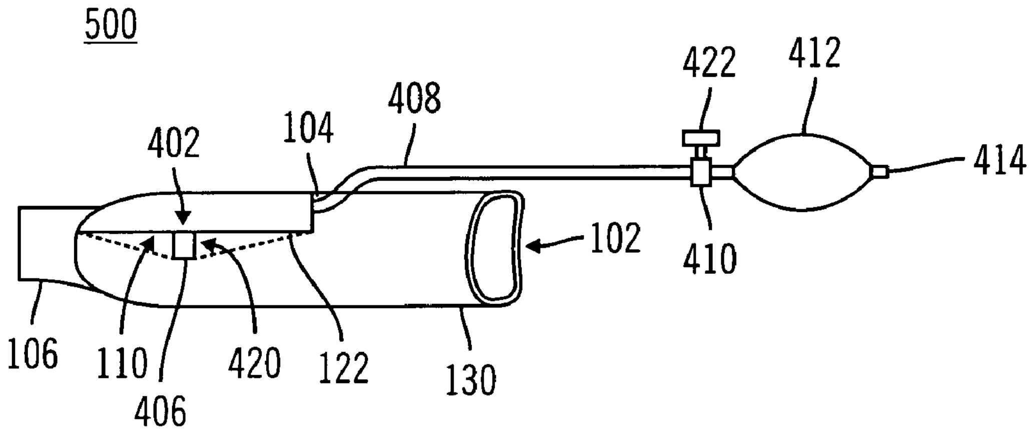
FIG. 5 illustrates a cut away view of the interior of the glove in accordance with the exemplary embodiment of the present invention.

FIG. 5 illustrates an interior view 500 of the glove 130 in accordance with the exemplary embodiment of the present invention. The interior view 500 is seen as looking into the wrist opening 102. The interior view 500 shows the bladder 402 and PPA 420, with button 406 facing towards the user's hand, inside pouch 110 inside the glove 130. Tube 408 is shown to exit the glove 130 through wrist slot 104. This arrangement allows the PPA 420, with the button 406 facing the user's hand, to be pressed into the user's hand with pressure supplied by bladder 402.

Figure 6:
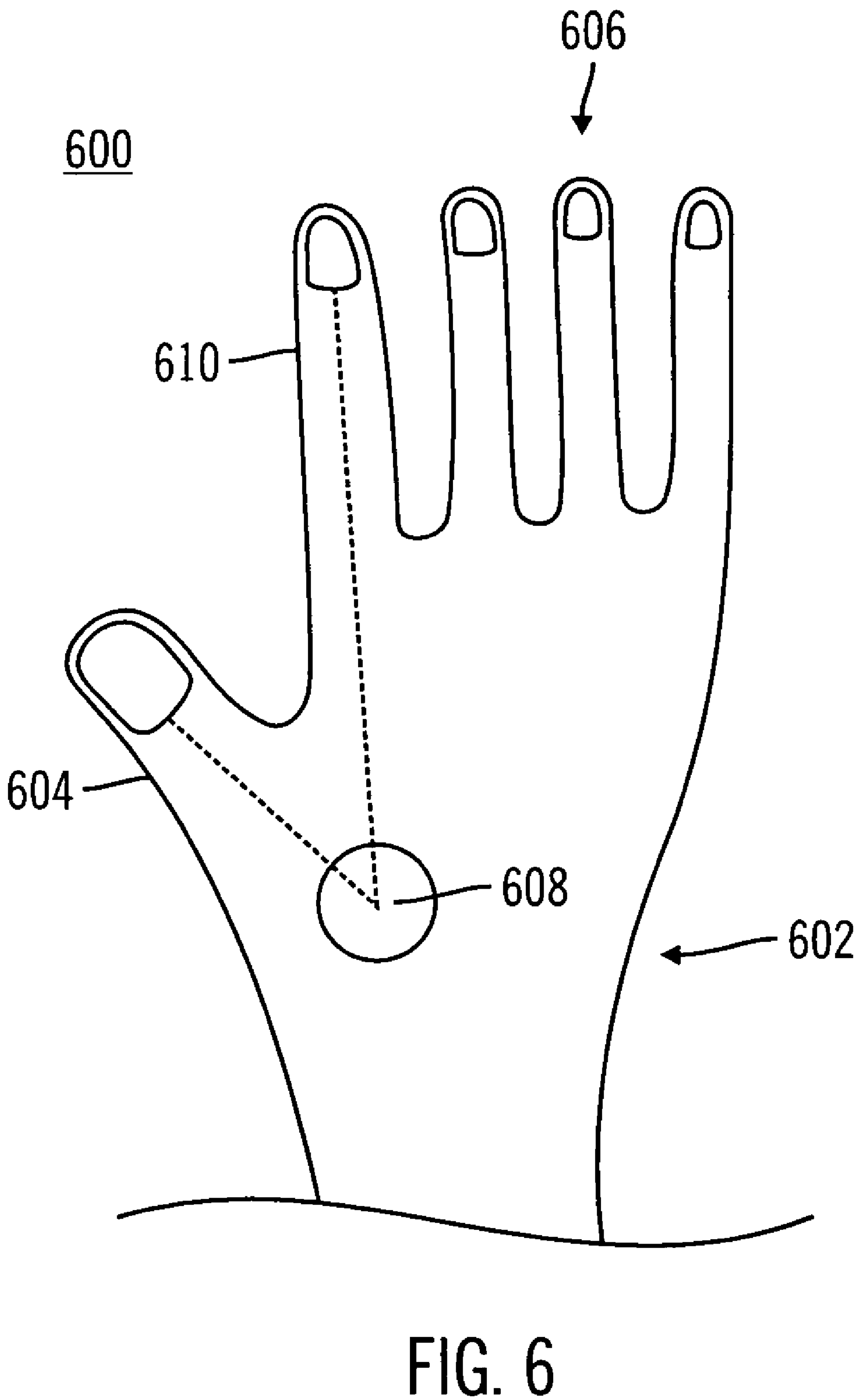
FIG. 6 illustrates back view of a user's hand with portions relevant to the operation of the present invention.

FIG. 6 illustrates back view of a user's hand 600 with portions relevant to the operation of the present invention. A user's hand 602 is shown to have a thumb 604 and four remaining fingers 606, including index finger 610. The Hegu pressure point 608 and operation of the glove 130 of the exemplary embodiment in relation to the Hegu point is discussed in detail below.

Figure 7:
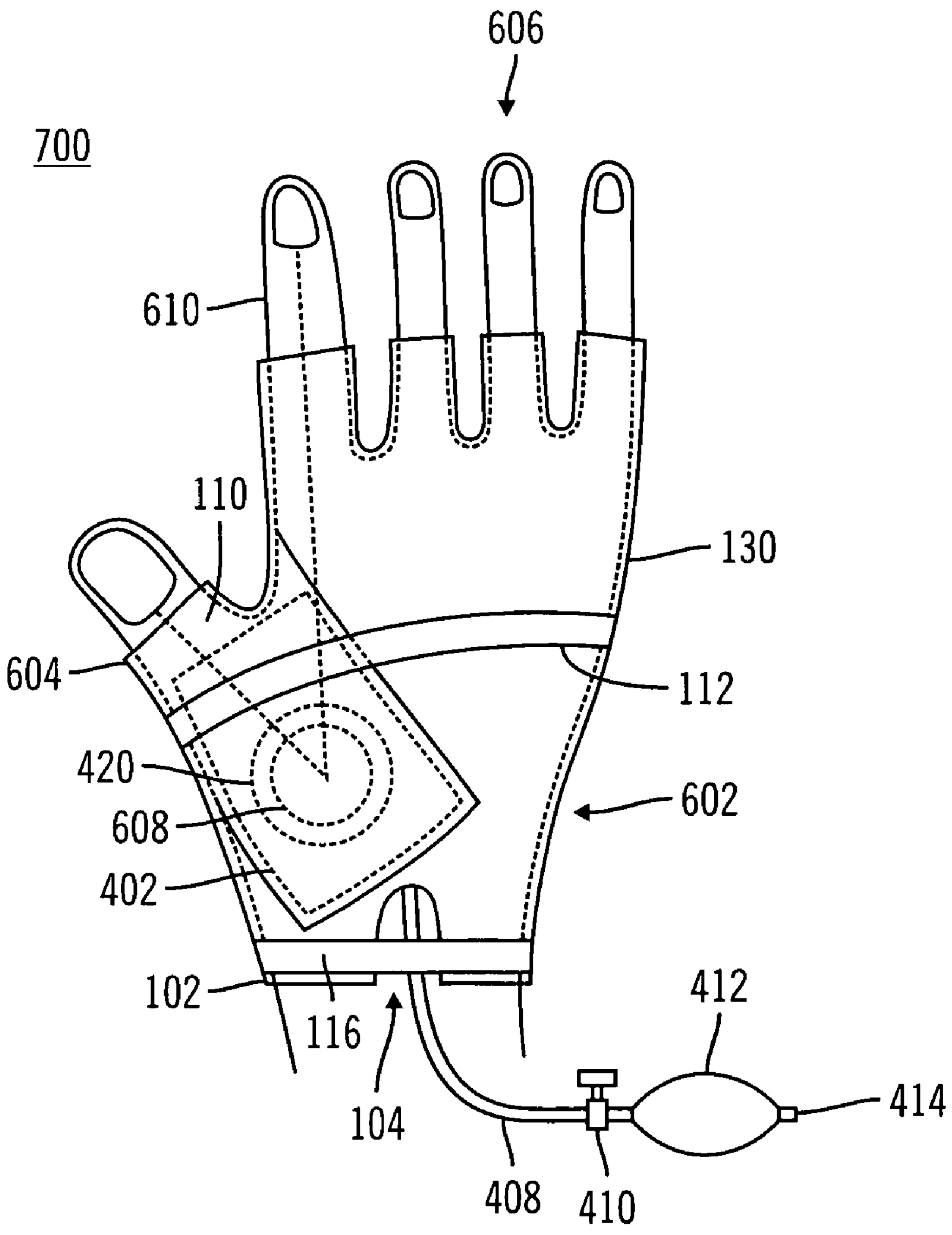
FIG. 7 illustrates the back of user's hand as it is located within the glove according to an exemplary embodiment of the present invention.

FIG. 7 illustrates the back of user's hand 600 as it is within glove 130 according to an exemplary embodiment of the present invention. The Hegu point '608 is shown as under the PPA 420 and bladder 402 is placed within pouch 110 of glove 130. The tube 408 exits the wrist slot 104. Wrist strap 116 and palm strap 112 are shown as closed to ensure proper placement of the glove 130 and the bladder 402/PPA 420 in particular. In operation, the user operates pump 412 to inflate the bladder 402 and apply pressure to his or her Hegu point 608 with the PPA 420. After use, the user operates valve 410 to release air from bladder 402 to remove pressure from the Hegu point 608.

Construction of the Exemplary Embodiment

The shell of glove 130 of the exemplary embodiment is made of Spandex. Various materials were tested, such as leather, mesh, nylon, varying percentages of Lycra, neoprene, and polyester using varying thicknesses, fabric density, and quality. Spandex was chosen based on an improved ability to control the positioning of the Bladder 402 and PPA 420. Spandex was further found to have superior comfort, durability, and ability to conform to varying hand densities with essentially the same hand size. In essence, hand size is determined by the distance from a user's wrist crease to the tip of his or her fingers. The glove 130 is therefore required to compensate for the width and thickness of the user's hand. The operation of embodiments of the present invention has been found to be unaffected with gloves that have closed fingers and open fingers. Open fingers 108 are used in the exemplary embodiment of the present invention to allow for long finger nails. Sizes for gloves 130 of the exemplary embodiment are able to be constructed with a relatively few number of sizes, such as S, M/L, and XL, due to the adaptive properties of the Spandex material used for the glove 130 of the exemplary embodiment. The use of some alternative materials might require additional sizes, such as XS, S, M, L, & XL. These sizes compensate for different hand sizes and thicknesses. The gloves 130 of the exemplary embodiment are chosen to be right handed due to a desire for consistency of stocked product. The effectiveness of the exemplary embodiment is not compromised by using gloves 130 that are left or right handed, including having a left handed person using a right handed glove 130. Further embodiments of the present invention use left handed gloves. Such left handed gloves might be required to accommodate those with special needs, such as amputees, persons with deformities, stroke victims, etc.

The two straps, wrist strap 106 and palm strap 112, approximately 6" in length with a 1" Velcro strip that is approximately 3" long. These two straps are attached by sewing the free end of the strap to the glove 130. These two straps are also made of spandex in the exemplary embodiment. Both straps are attached by sewing to the pinky side of the glove (the ridge of the hand representing the lateral aspect of the 5th metacarpal).

The wrist strap 116 is attached at the crease of the wrist portion of glove 130. The wrist strap 116 is used to secure the filler tube 408 and assist in stabilizing the bladder 402 within pouch 110. The wrist strap 116 wraps around the wrist and attaches to the wrist section Velcro strip 120, which is the other half of the Velcro strip that is attached by sewing it to the bottom side of the glove (posterior aspect of the distal end of the lower arm or the palm side of the wrist). The wrist section Velcro strip 120 of the exemplary embodiment is one inch long. The palm strap 112 is attached approximately at the location where the middle of the 5th metacarpal will fit into the glove. The palm strap 112 is placed across the dorsum of the hand and over the back of the pouch 110 and therefore the bladder 402. The palm strap 112 wraps around the middle of the 1st metacarpal (or the base of the thumb) and attaches to the palm area Velcro strip 302 that is sewn into the palm of the glove 130. The angle at which the palm area Velcro strip 302 is placed helps secure the positioning of the palm strap 112 so that its is placed so as to cover the Bladder 402/PPA 420 by extending directly over the middle of the bladder. Palm strap 112 was further designed to help reduce the amount of air needed in the bladder 402 to apply enough pressure on the PPA 420 to be effective. Reducing the amount of air in the bladder 402 accomplishes two things: first, the bladder 402 does not have to be filled up so big that it looks scary, and second, this also helps control movement of the bladder 402 after it has been inflated. The palm strap 112 that covers the dorsum of the hand and the bladder is able to be embroidered with a logo. The glove 130 of the exemplary embodiment is made in a blue color because studies involving color therapy state that blue is a stress relieving color. For example, Peter Mendall, the founder of Color Puncture, lives in Germany and has documented healing terminal diseases using color puncture. One of the main colors that his research has found to be most consistent in his treatments was the color blue. (Especially the mid spectrum)

A pouch 110 that is sewn on the inside of the glove 110 is at the side of the glove where the glove lays on the dorsum of the hand. This pouch 110 holds the Bladder 402 PPA 420. It is also constructed of a blue spandex in the exemplary embodiment. Proper placement of the pouch 110 supports the proper placement of the PPA 420 when the glove 130 is worn. The size of the 110 pouch helps control the bladder 402 from rolling over or coming out of the glove. The initial positioning of the bladder 402 helps reduce the amount of movement needed for positioning of the PPA 420 after the glove 130 is put on.

Components

The bladder 402 of the exemplary embodiment is made of a rubber that has been approved by the FDA for food preparation. This reduces the risk that contact with the skin might cause any adverse reactions. The bladder 402 of the exemplary embodiment is specifically designed to pull in the far end and the sides, thereby causing direct pressure in the up and down direction. This action causes the top of the bladder to press against the inside of the glove 130 and the palm strap 112. The bottom side of the bladder 402 that has the PPA 420 attached to it pushes straight down onto the desired point on the web of the hand 602. The design of the bladder avoids applying pressure to the dorsum of the hand. This excessive pressure can cause the index finger 610 to feel numb and may result in some discomfort. The filler tube 408 is selected to be 1841 long and has a ⅛" wall for flexibility. The length of the filler tube 408 was selected based upon an average of the distance from the crease of a person's wrist to the person's opposite hand when placed across his or her lap.

The bladder 402 of the exemplary embodiment is a pressure applicator and further presses the PPA 420 into the wearer's hand 602 with a yieldable force that improves comfort for the wearer and allows for movement of the wearer's hand 602 while applying a substantially constant force. Alternative embodiments provide a fixed arrangement, such as a C-clamp style force applicator, but do not accommodate movement of the wearer's hand and therefore can create discomfort by exerting excessive forces for some positions of the wearer's hand.

A Pressure Point Applicator 420 of the exemplary embodiment is made of stainless steel and is preferably shaped like a button with a base. The button 406 is 0.250" dia., the base is 0.750" dia., the height of the button is 0.437". The thickness of the base plate 404 is 0.062". The top of the button 406 is a full radius. The use of a full radius on the top of the button 406 improves the comfort for the wearer. These measurements are strongly related to the amount of pressure that is applied to the web of the hand by the glove and can impact the safeness of the use of the glove. These shapes and dimensions were arrived at by the inventor after testing hundreds of sizes and shapes, including different types of materials.

The pump bulb 412 that is used to inflate the bladder 402 is made of a soft synthetic material that is easy to squeeze or compress. The pump bulb 412 fills the bladder 402 with air each time the pump bulb 412 is compressed. The pump bulb 412 of the exemplary embodiment works with the slightest amount of pressure applied. The valve 110 allows you to control the amount of air in the bladder by simply turning a knurled knob 422 to the right to close the valve 110 and hold the air in the bladder 402 or release the air in the bladder 402 by turning the knob 422 to the left. The amount that the valve is turned to the left determines how fast the air is released from the bladder 402.

Figure 16:
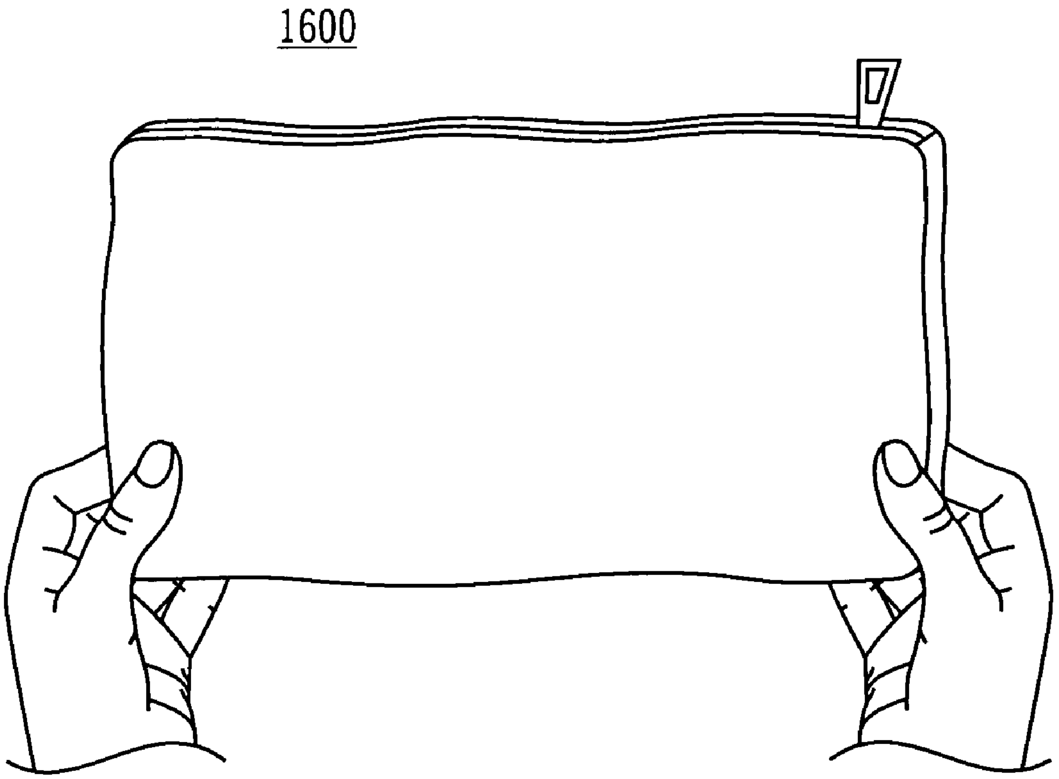
FIG. 16 illustrates a carrying case for the glove and associated materials.

The exemplary embodiment further includes a carrying case that is shown in FIG. 16. The case is made of polyester and has an 8" plastic zipper. This case is also able to be embroidered with a logo. The case is preferably 6"×9".

Summary of Assembly

The PPA 420 of the exemplary embodiment is attached to the bladder 402 by over-lapping the base 404 of the PPA 420 with a flap made of the same material as the bladder 402. The PPA 420 is attached so as to allow the button portion 406 of the PPA 420 to be exposed. One end of the filler tube 408 is attached to the end of the bladder 402 and the other end of the filler tube 408 is attached to the valve 110 of the pump bulb 412. The other end of the valve 110 is attached to the pump bulb 112. The bladder 112 is placed into the pouch 110 that has been sewn into the dorsum part of the glove 130. The secure fit provides for easy positioning of the PPA 420 when the glove 130 is placed on the hand 602. The Velcro straps are preferably attached while the glove 130 is stored in the carrying case.

Usage of the Glove

First Step: Priming the Point: Proper operation of the exemplary embodiment begins by the user finding the Hegu point 608 of his or her hand. In order to find the Hegu point 608 and thereby "prime the point," the user finds two bones within his or her hand 608. A first bone is the bone going to his or her thumb 604 and the other bone is the bone going to his or her index finger 610. The user then follows these bones up towards the user's wrist until they meet. Just in front of this point is Hegu point 608, located at the beginning to the web of the user's hand 602. The user primes the Hegu point by squeezing this point with his or her index finger and thumb for 10 seconds.

Figure 8:
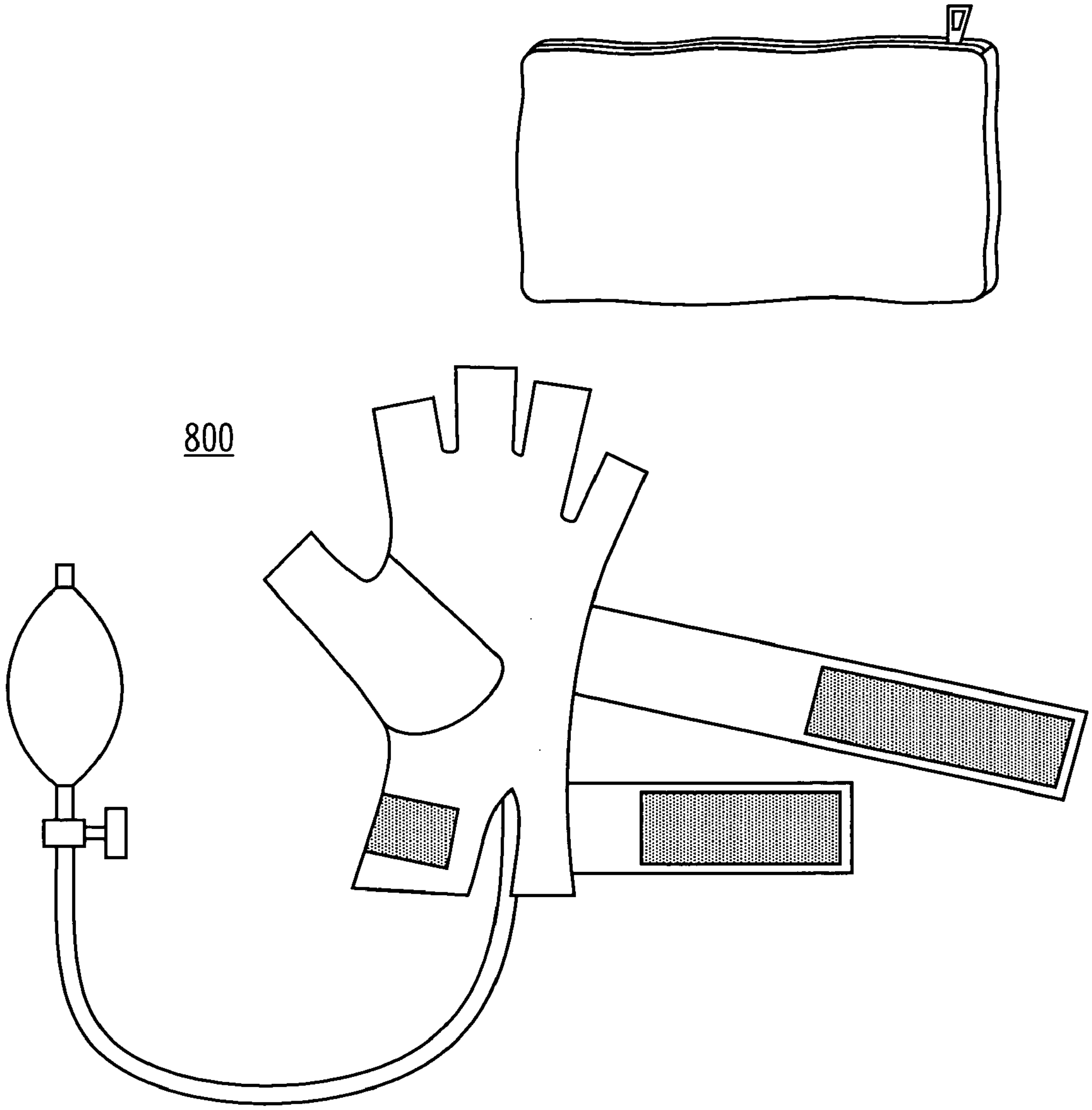
FIG. 8 illustrates a prepared glove that is ready for use.
Figure 9:
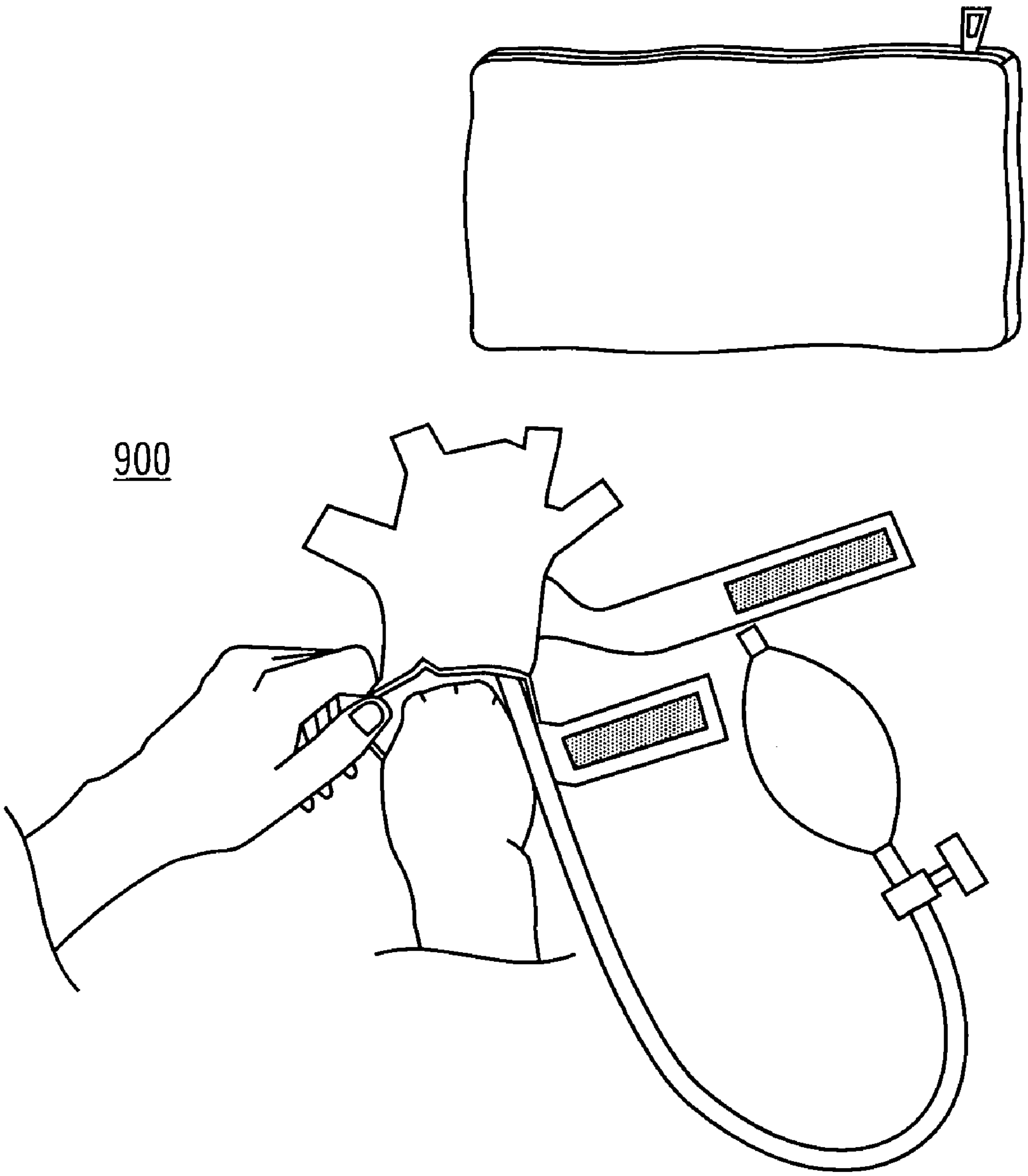
FIG. 9 illustrates a user putting on the glove.

Second Step: Preparing the Glove: FIG. 8 illustrates a prepared glove 800 that is ready for use. The straps, i.e., wrist strap 116 and palm strap 112, of the glove 130 are opened. The user should ensure that the Velcro that is sewn onto the glove is facing down. FIG. 9 illustrates a user putting on the glove 900.

Figure 10:
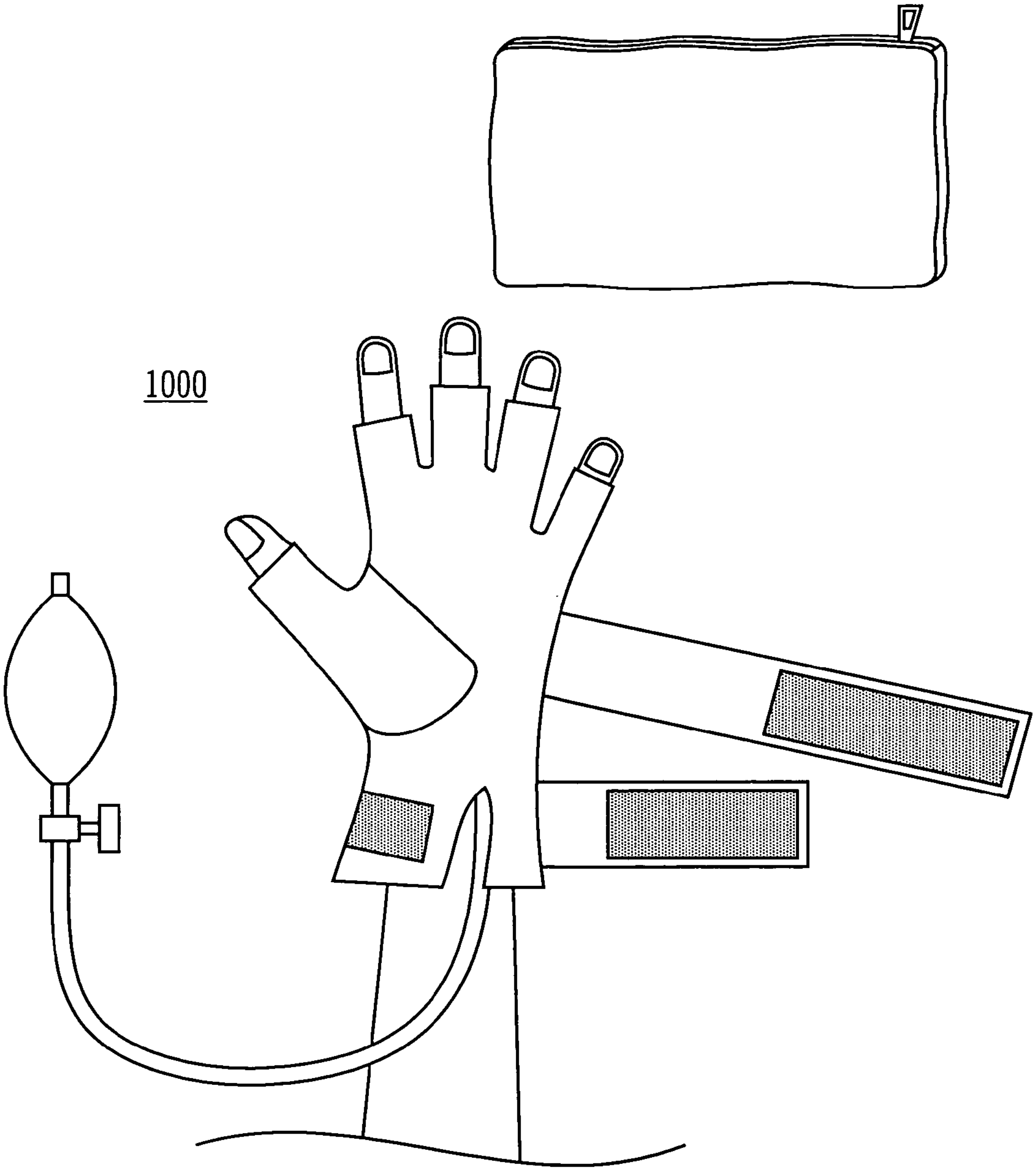
FIG. 10 illustrates a worn glove ready for closure.
Figure 11:
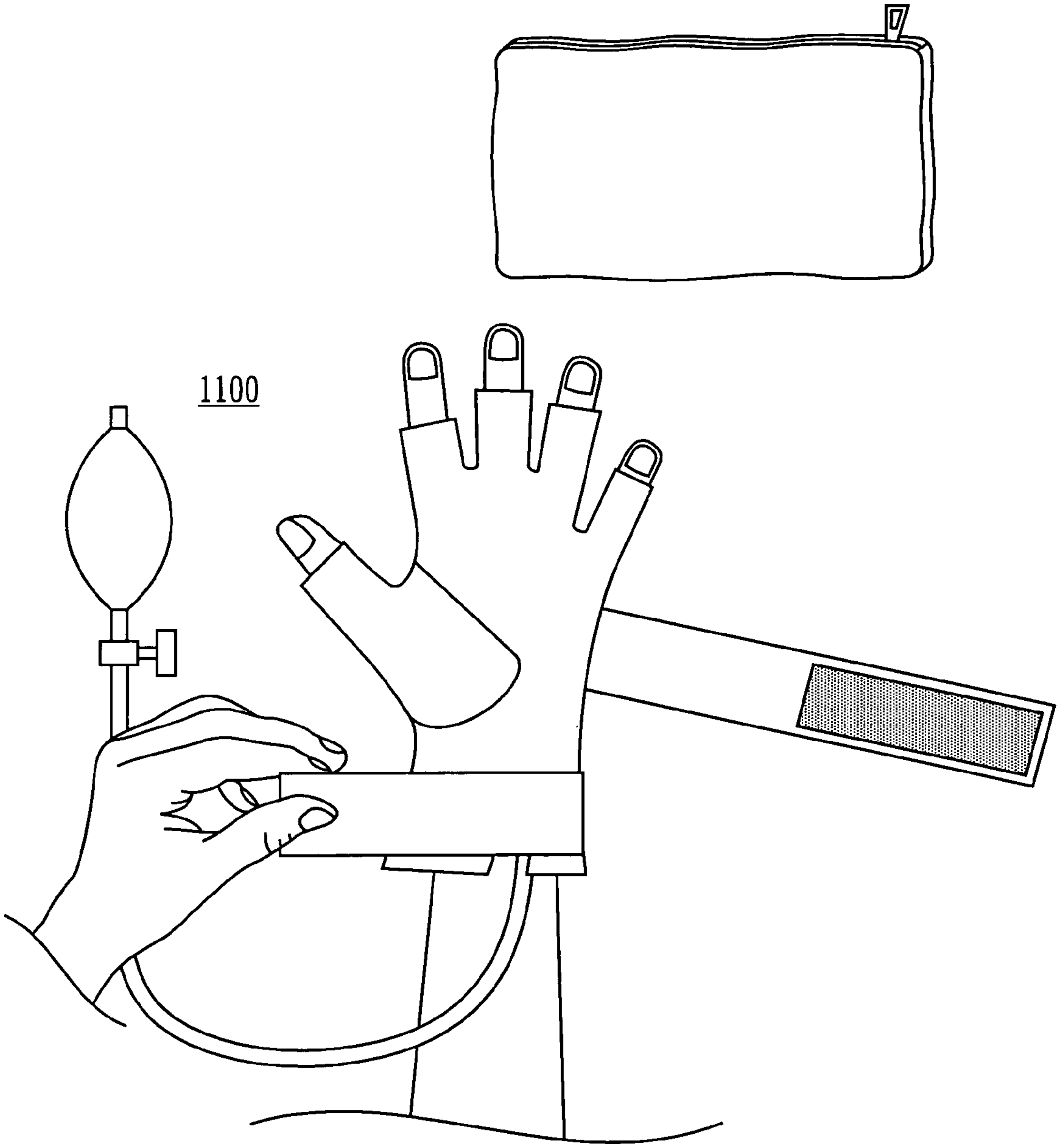
FIG. 11 illustrates closing the wrist strap comfortably.
Figure 12:
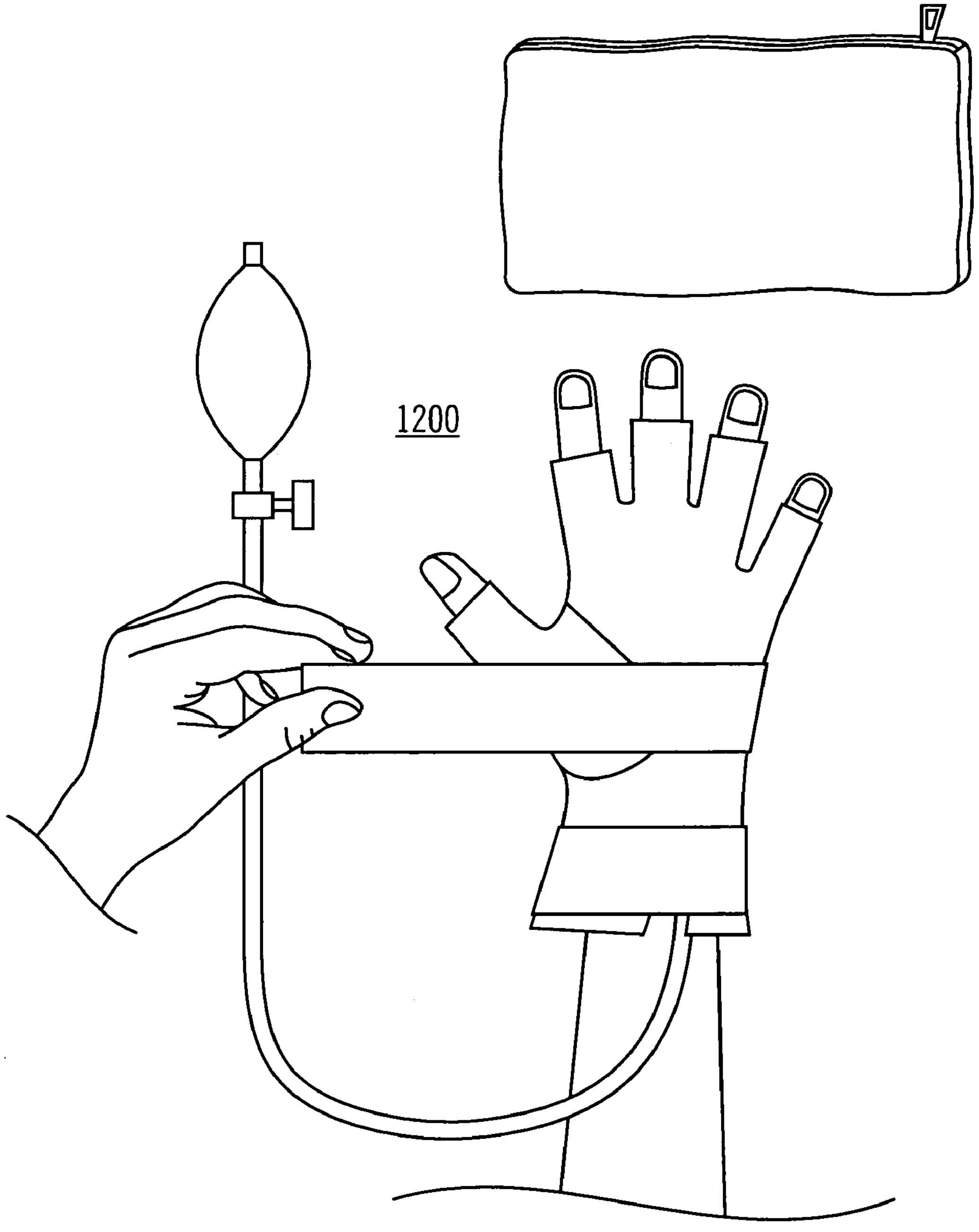
FIGS. 12 and 13 illustrate closing the palm strap.
Figure 13:
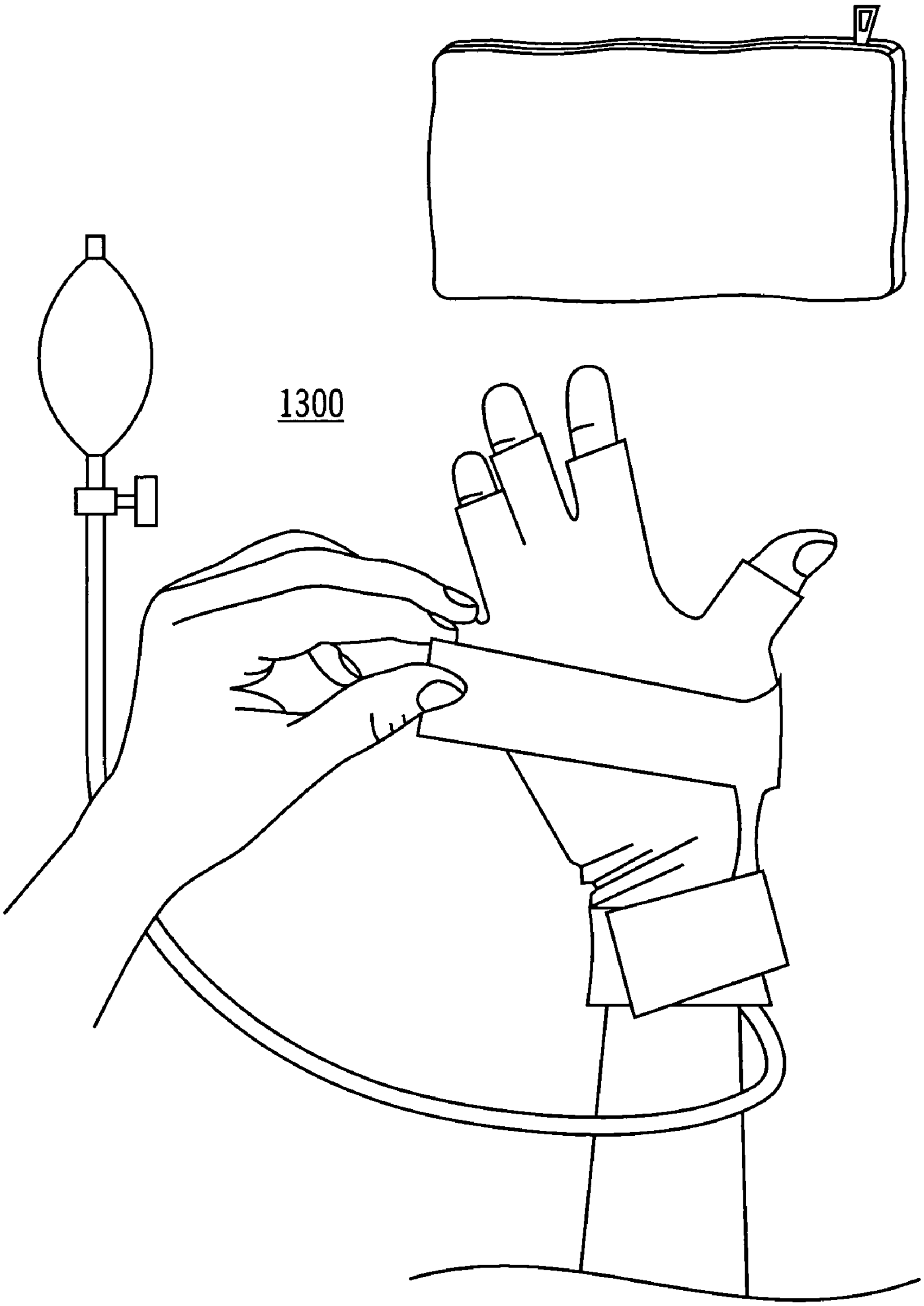

Third Step: Closing the Straps: FIG. 10 illustrates a worn glove ready for closure 1000. The user places the filler hose 408 across his or her lap. The user then closes the straps of the glove 130. FIG. 11 illustrates closing the wrist strap 116 comfortably. FIGS. 12 and 13 illustrate closing the palm strap 112 by placing it over the middle of the bladder 402 and attaching it to the palm area Velcro strip 302.

Figure 14:
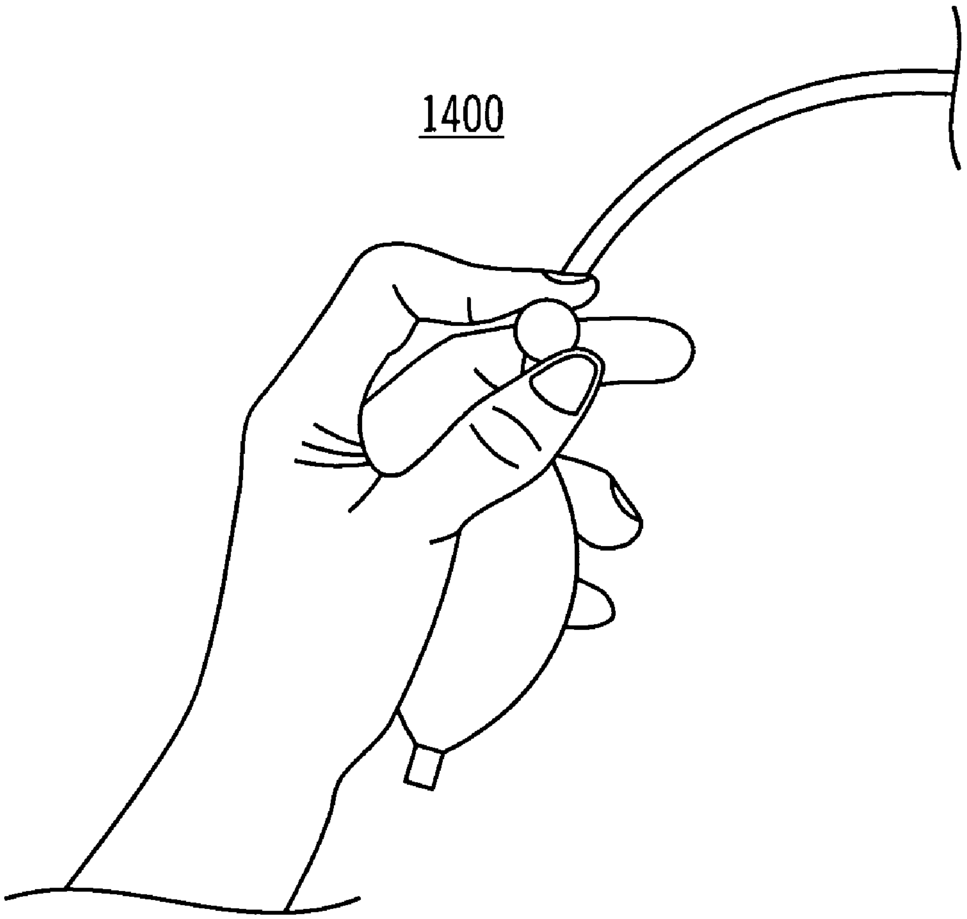
FIG. 14 illustrates operating the valve.
Figure 15:
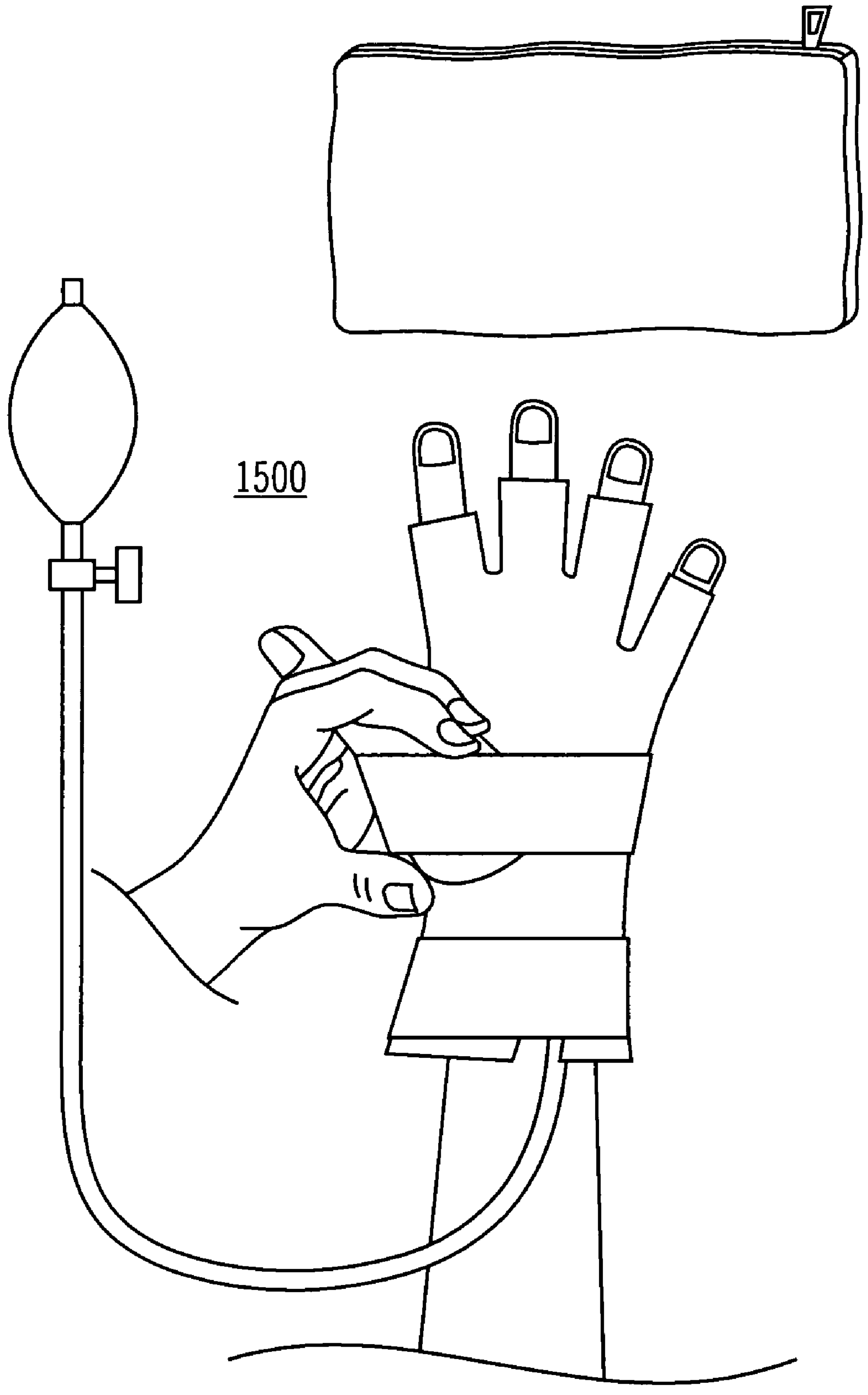
FIG. 15 illustrates positioning a properly placed glove.

Fourth Step: Securing the Position of the PPA: FIG. 14 illustrates operating the valve 1400. The user initially turns the knob 422 on the valve 410 to the right to close the valve 410 and cause the air to stay in the bladder 402. The user is recommended to squeeze the bulb 412 twice. FIG. 15 illustrates positioning a properly placed glove 1500. FIG. 15 specifically illustrates adjusting the position of the bladder 402 and PPA 420 once the glove 130 is on the user's hand. The user is now to make sure that the PPA 420 is felt in approximately the same place that he or she primed his or her hand, i.e., the Hegu point 608. The PPA 420 of the exemplary embodiment does not have to be in an exact spot to work, but should be in the general vicinity of the Hegu point 608. If the button 406 is touching one of the bones of the hand 602, it will feel uncomfortable. By simply pushing the side of the bladder 402 slightly, as is shown in positioning 1500, the user can easily and comfortably adjust the position of the PPA 420. The PPA 420 usually falls right into place. If it does not, it takes only the slightest movement to adjust the PPA's position.

Fifth Step: Applying Pressure: Sit back, try to relax. The user then squeezes the pump bulb 412 slowly; squeeze the pump bulb 412 one squeeze at a time. When the pressure is right, the user will feel his or her pulse in his or her hand. This is plenty of pressure for the glove to work.

Sixth Step: The user is to breathe in through his or her nose and out through his or her mouth, slowly. Relief will be felt soon and within a few minutes the headache will be gone.

When the headache has been completely relieved, turn the knob 422 on the valve 410 to the left to release the air in the bladder 402. FIG. 16 illustrates a carrying case for the glove 130 and associated materials. After use, the user is able to take off the glove 130 and place it back in the carrying case.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover applications, modifications, and embodiments within the scope of the present invention.

What is claimed is:

1. A method for relieving pain, the method comprising:

positioning a pressure point applicator over a desired point on the outside web of a wearer's hand;

positioning a pressure applicator on the pressure point applicator, wherein the pressure applicator comprises a glove worn over the wearer's hand, the glove further comprising an expandable bladder;

operating the expandable bladder so as to apply constant, user adjustable force to the pressure point applicator, wherein the constant, user adjustable force results in pressing the pressure point applicator into the outside web of the wearer's hand with a user adjustable constant force that is substantially perpendicular to the outside web of the wearer's hand.

2. The method of claim 1, wherein the pressure point applicator comprises a button mechanically coupled to and protruding from the expandable bladder.

3. The method of claim 1, wherein the glove comprises a palm strap placed over the expandable bladder.

4. The method according to claim 1, wherein the expandable bladder is operated by a hand pump.

5. An apparatus for relieving pain, the apparatus comprising:

a pressure point applicator for applying pressure to a particular point on the outside web of a person's hand; and a pressure applicator, mechanically coupled to the pressure point applicator, the pressure applicator comprising a glove worn over the wearer's hand and an expandable bladder, wherein the expandable bladder operates to apply constant, user adjustable force to the pressure point applicator and wherein the constant, user adjustable force results in pressing the pressure point applicator into the outside web of the person's hand with a user adjustable constant force that is substantially perpendicular to the outside web of the wearer's hand.

6. The apparatus of claim 5, wherein the pressure point applicator comprises a button mechanically coupled to and protruding from the expandable bladder.

7. The apparatus of claim 5, further comprising at least one strap placed over the pressure applicator.

8. The apparatus of claim 5, wherein the expandable bladder is user inflatable to provide a user desired amount of force to the outside web of the person's hand.

9. The apparatus according to claim 5, further comprising a hand pump that operates the expandable bladder.

10. The apparatus according to claim 9, wherein the hand pump comprises a valve that holds air in the expandable bladder and releases air from the expandable bladder.

11. The apparatus according to claim 5, wherein the expandable bladder is contained within a pocket within the glove.

12. The apparatus according to claim 6, wherein the expandable bladder and at least a portion of the button is contained within a pocket within the glove.

13. The apparatus according to claim 6, wherein the glove is formed of spandex.

14. The apparatus according to claim 12, wherein the glove is formed of blue spandex.

15. An apparatus for relieving pain, the apparatus comprising:

a glove worn over a wearer's hand;

a pressure point applicator, mounted within the glove, that applies force to a particular point on the outside web of a person's hand;

an expandable bladder, mounted within the glove and mechanically coupled to the pressure point applicator, the expandable bladder operating to apply a constant, user adjustable pressure to the pressure point applicator and wherein the constant user adjustable pressure results in pressing the pressure point applicator into the outside web of the person's hand with a constant user adjustable force that is substantially perpendicular to the outside web of the wearer's hand; and a hand operated pump, in pneumatic communication with the expandable bladder, the hand operated pump being able to be operated by the wearer and operating to adjust pressure within the expandable bladder.

* * * * *